United States Patent [19]

Khokhar et al.

[11] Patent Number: 5,288,887
[45] Date of Patent: Feb. 22, 1994

[54] DIAMINE PLATINUM(IV) COMPLEXES HAVING MIXED CARBOXYLATE LIGANDS AS ANTITUMOR AGENTS

[75] Inventors: Abdul R. Khokhar; Zahid H. Siddik; Salaam Al-Baker, all of Houston, Tex.

[73] Assignee: Board of Regents, The University Texas System, Austin, Tex.

[21] Appl. No.: 978,788

[22] Filed: Nov. 19, 1992

Related U.S. Application Data

[60] Continuation-in-part of Ser. No. 927,201, Aug. 7, 1992, which is a continuation-in-part of Ser. No. 624,795, Dec. 7, 1990, abandoned, which is a division of Ser. No. 274,824, Nov. 22, 1988, Pat. No. 5,041,578.

[51] Int. Cl.$^5$ .................. C07F 15/00; A61K 31/28
[52] U.S. Cl. ..................................... 556/137; 540/465
[58] Field of Search ............... 556/137; 514/184, 185, 514/492; 540/465

[56] References Cited

U.S. PATENT DOCUMENTS

| | | | |
|---|---|---|---|
| 3,904,663 | 9/1975 | Tobe et al. | 260/429 R |
| 4,115,418 | 9/1978 | Gale et al. | 260/429 R |
| 4,137,248 | 1/1979 | Gale et al. | 260/429 R |
| 4,140,707 | 2/1979 | Cleare et al. | 260/429 R |
| 4,169,846 | 10/1979 | Kidani et al. | 260/429 R |
| 4,203,912 | 5/1980 | Hydes et al. | 260/429 R |
| 4,225,529 | 9/1980 | Hydes et al. | 260/429 R |
| 4,230,631 | 10/1980 | Hydes et al. | 260/429 R |
| 4,256,652 | 3/1981 | Kidani et al. | 260/429 R |
| 4,271,085 | 6/1981 | Amundsen et al. | 260/429 R |
| 4,431,666 | 2/1984 | Bulten et al. | 424/287 |
| 4,466,924 | 8/1984 | Verbeek et al. | 260/429 R |
| 4,614,811 | 9/1986 | Gandolfi | 556/137 |
| 4,657,927 | 4/1987 | Cleare et al. | 514/492 |
| 4,661,516 | 4/1987 | Brown et al. | 514/492 |
| 4,680,308 | 7/1987 | Schwartz et al. | 514/492 |
| 4,716,157 | 12/1987 | Bitha et al. | 514/184 |
| 4,760,155 | 7/1988 | Heffernan et al. | 556/136 |
| 4,760,156 | 7/1988 | Heffernan et al. | 556/136 |
| 4,760,157 | 7/1988 | Child et al. | 556/137 |
| 4,845,124 | 7/1989 | Kidani et al. | 514/492 |
| 4,861,905 | 8/1989 | Nowatari et al. | 556/40 |
| 5,206,400 | 4/1993 | Witiak et al. | 556/137 |

FOREIGN PATENT DOCUMENTS

| | | |
|---|---|---|
| 569425 | 1/1988 | Australia . |
| 898614 | 5/1984 | Belgium . |
| 0113508 | 7/1984 | European Pat. Off. . |
| 0130482 | 1/1985 | European Pat. Off. . |
| 0136012 | 4/1985 | European Pat. Off. . |
| 0147926 | 7/1985 | European Pat. Off. . |
| 0193936 | 9/1986 | European Pat. Off. . |
| 0237450 | 9/1987 | European Pat. Off. . |
| 2160867A | 1/1986 | United Kingdom . |
| WO87/02364 | 4/1987 | World Int. Prop. O. . |
| WO88/03925 | 6/1988 | World Int. Prop. O. . |

OTHER PUBLICATIONS

Perez-Soler et al., "Treatment and Prophylaxis of Experimental Liver Metastases of M5076 Reticulosarcoma with cis-Bis-neodecanoato-trans-R,R-1,2-diaminocyclohexaneplatinum(II) Encapsulated in Multilamellar Vesicles", Cancer Research, 47:6462–6466 (Dec. 1987).

Maeda, et al., "Liposoluble Platinum(II) Complexes with Antitumor Activity", Japan Journal Cancer Research, 77:523–525 (Jun. 1986).

(List continued on next page.)

*Primary Examiner*—Arthur C. Prescott
*Attorney, Agent, or Firm*—Arnold, White & Durkee

[57] ABSTRACT

Platinum(IV) complexes with mixed carboxylato ligands having the formula:

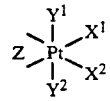

where $X^1$ and $X^2$ are carboxylato, or are jointly dicarboxylato, where $Y^1$ and $Y^2$ are carboxylato, and where Z is either diaminocyclohexane or ethylenediamine, have been found to have desirable antitumor activity, as well as relatively low levels of toxicity.

12 Claims, No Drawings

OTHER PUBLICATIONS

Vollano et al., "Comparative Antitumor Studies on Platinum(II) and Platinum(IV) Complexes Containing 1,2-Diaminocyclohexane", J. Med. Chem., 30:716–719 (1987).

Belg. BE 898,614, "Cis-1,2-Diaminocyclohexane Platinum Complexes", Chem. Abstracts 101:177510w (1984).

Kihari, "Organoplatinum Complexes as Antineoplastics", Chemical Abstracts 105:134160X (1989).

Craciunescu, "On the Preparation, Antitumor and Cyctotoxic Evaluation of Some New Analogues of the Cis-Dichloro (1,2-Diamino-Cyclohexane) Platinum-(II) Complex", Eur. J. Med. Chem., 4:353–357 (1984).

Sur, "Effect of Liposomal Encapsulation of Cis–Platinum Diamminodichloride in the Treatment of Ehrlich Ascites Carcinoma", Oncology, 40:372–376 (1983).

Freise, "Pharmacokinetics of Liposome Encapsulated Cisplatin in Rats", Archives etc., 258:180–192 (1982).

Kaledin, "Intralymphatic Administration of Liposome-Encapsulated Drugs to Mice: Possibility for Suppression of the Growth of Tumor Metastases in the Lymph Nodes", JNCL, 66:881–886 (1981).

Deliconstantinos, "Incorporation of Cis-Dichlorobis-cyclopentylamineplatinum (II) into Liposomes Enhances its Uptake by ADJ/PC6A Tumors Implanted Subcutaneously into Mice", Biochem. Soc. Trans., 5:1326–1328 (1977).

Yatvin, "Selective Delivery by Hyperthermia of Liposome Encapsulated Cis Dichlorodiamine Platinum(II) and Tumor Growth Delay" (Meeting Abstract) Proc. Am. Assoc. Cancer Res., 21:281 (1980).

Schwartz, "Preparation and Antitumor Evaluation of Water-Soluble Derivatives of Dichloro(1,2-diaminocyclohexane)platinum(II)", Chemical Abstracts, 88:16014K (1978).

Perez-Soler, "Toxicity and Antitumor Activity of cis-Bis-cyclopentenecarboxylato-1,2-diaminocyclohexane Platinum(II) Encapsulated in Multilamellar Vesicles", Cancer Research 46, 6269–6273 (1986).

Connors, "New Platinum Complexes with Anti-Tumor Activity", Chem. Biol. Interactions, 5:415–424 (1972).

Ridgway, "Analogs of Sulfato 1,2-Diaminocyclohexane Platinum(II). I. Modifications in Leaving Ligand", J. Clin. Hematol. Oncol. 7:220–229 (1977).

Burchenal, "Rationale of Combination Chemotherapy", Chemical Abstracts 93:125661t (1980).

Appleton, "Reactions of Platinum(II) Aqua Complexes", Chemical Abstracts 101:182656c (1984).

Speer, "Malonato-1,2-diaminocyclohexaneplatinum-(II), a Potential Antitumor Agent", Chemical Abstracts 84:54030n (1976).

Khokhar, "The Synthesis and Antitumor Properties of a Series of Water Soluble Carboxylato(1,2-diaminocyclohexane)platinum(II) Complexes", Chemical Abstracts 103:226308p (1985).

Tzu, "Synthesis and Study of Some Platinum Complexes with Dicarboxylic Acids", Chemical Abstracts 94:218774t (1981).

DIAMINE PLATINUM(IV) COMPLEXES HAVING MIXED CARBOXYLATE LIGANDS AS ANTITUMOR AGENTS

The U.S. government owns certain right in this invention.

This patent application is a continuation-in-part of U.S. Ser. No. 07/927,201, filed on Aug. 7, 1992, now pending, which was a continuation-in-part of U.S. Ser. No. 07/624,795, filed on Dec. 7, 1990, now abandoned, which was a divisional of U.S. Ser. No. 07/274,824, filed on Nov. 22, 1988, now issued as U.S. Pat. No. 5,041,578. All of the above patents and patent applications are incorporated here by reference.

FIELD OF THE INVENTION

The present invention relates to platinum based drugs and methods of using such drugs and formulations thereof in antitumor therapy.

BACKGROUND OF THE INVENTION

Some platinum based drugs are known to have useful antitumor activity. However, such drugs are also known to have various problems. For example, cis-diamminedichloroplatinum(II), also referred to as cisplatin or CDDP, is one such drug with a significant level of activity, but which also exhibits significant nephrotoxicity and other harmful side effects. Other platinum drugs have been synthesized which have less potential to cause renal injury, but many of these drugs are much less soluble in water than is desirable.

A long standing need exists for platinum drugs which have improved aqueous solubility and antitumor activity, a broad spectrum of activity against various neoplastic disease states, reduced toxicity, and a lack of cross resistance to other antitumor drugs such as cisplatin.

SUMMARY OF THE INVENTION

The present invention relates to platinum(IV) complexes having the formula

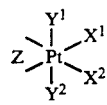

and stereoisomers thereof, where $X^1$ and $X^2$ are carboxylato ligands, or are jointly a dicarboxylato ligand, $Y^1$ and $Y^2$ are carboxylato ligands, and Z is a bidentate amino ligand selected from the group consisting of diaminocyclohexane and ethylenediamine. $X^1$ and $X^2$ can be different carboxylato ligands than $Y^1$ and $Y^2$. When $X^1$ and $X^2$ are monocarboxylato, they preferably have between about 1–10 carbon atoms each. When $X^1$ and $X^2$ are jointly dicarboxylato, they preferably have between about 2–20 carbon atoms. Likewise, when $Y^1$ and $Y^2$ are monocarboxylato, they preferably have between about 1–10 carbon atoms each.

Examples of suitable carboxylato ligands include acetato, trifluoroacetato, cyclobutanecarboxylato, 1,1-cyclobutanedicarboxylato, oxalato, malonato, methylmalonato, ketomalonato, and tartronato.

The present invention also concerns antitumor compositions which include an effective amount of one or more above-described complexes, and a pharmaceutically acceptable carrier. Additionally, the present invention concerns methods of inhibiting neoplastic cell growth, which include the step of administering to a mammal an effective amount of one or more of the above-described complexes.

The complexes, compositions, and methods of the present invention possess significant advantages over the prior art. Platinum (IV) complexes in accordance with the present invention possess high aqueous solubility, high antitumor activity (greater against some tumor models than cisplatin and carboplatin), a broad spectrum of activity, and a lack of cross resistance to other antitumor drugs such as cisplatin. Therefore, the complexes, compositions, and methods of the present invention are believed to have significant therapeutic advantages in the treatment of neoplastic disease states, including the specific cancers of the testes, ovaries, bladder, and head and neck.

DETAILED DESCRIPTION OF SPECIFIC EMBODIMENTS

Synthesis

A number of diaminocyclohexane (DACH) complexes, listed in Table 1 below, were synthesized, having the general formula:

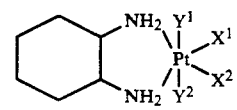

TABLE 1

| Complex No. | Complex Name | Elemental Analysis of DACH—Pt(IV) Complexes Observed (Calculated) | | |
|---|---|---|---|---|
| 1. | (Trans-R,R-1,2-diaminocyclohexane)-(tetraacetato)platinum(IV) | 30.79(30.82) | 4.86(4.77) | 4.92(5.13) |
| 2. | (Trans-S,S-1,2-diaminocyclohexane)-(tetraacetato)platinum(IV) | 30.45(30.82) | 4.84(4.77) | 4.81(5.13) |
| 3. | (Cis-1,2-diaminocyclohexane)-(tetraacetato)platinum(IV) | 30.11(30.82) | 4.93(4.73) | 4.75(5.13) |
| 4. | Cis-diacetato(trans-R,R-1,2-diaminocyclohexane)trans-bis(trifluoroacetato)platinum(IV).H$_2$O | 24.66(25.03) | 2.57(3.27) | 4.09(4.17) |
| 5. | Trans-diacetato(trans-R,R-1,2-diaminocyclohexane)cis-bis(trifluoroacetato)platinum(IV) | 25.42(25.72) | 4.23(3.06) | 4.82(4.28) |
| 6. | Trans-diacetato(trans-R,R-1,2-diaminocyclohexane)cis-bis(cyclobutanecarboxylato)platinum(IV).H$_2$O | 37.13(37.32) | 5.29(5.59) | 4.24(4.35) |
| 7. | Trans-diacetato(trans-S,S-1,2- | 39.01(38.40) | 5.46(5.44) | 4.06(4.48) |

TABLE 1-continued
Elemental Analysis of DACH—Pt(IV) Complexes

| Complex No. | Complex Name | Observed (Calculated) | | |
|---|---|---|---|---|
| | diaminocyclohexane)cis-bis(cyclo-butanecarboxylato)platinum(IV) | | | |
| 8. | Trans-diacetato(cis-1,2-diamino-cyclohexane)-bis(cyclo-butanecarboxylato)platinum(IV).H$_2$O | 37.34(37.32) | 5.51(5.59) | 4.18(4.35) |
| 9. | Cis-bis(cyclobutanecarboxylato)-(trans-R,R-1,2-diaminocyclohexane)-trans-bis(trifluoroacetato)platinum(IV).H$_2$O | 31.19(31.95) | 3.58(3.99) | 3.76(3.72) |
| 10. | Trans-diacetato(trans-R-R-1,2-diaminocyclohexane)oxalatoplatinum(IV) | 27.71(27.96) | 4.17(3.88) | 5.23(5.43) |
| 11. | Trans-diacetato(trans-S,S-1,2-diaminocyclohexane)oxalatoplatinum(IV).H$_2$O | 27.06(27.01) | 4.15(4.12) | 5.13(5.25) |
| 12. | Trans-diacetato(cis-1,2-diamino-cyclohexane)oxalatoplatinum(IV).2H$_2$O | 26.00(26.13) | 4.06(4.35) | 5.34(5.08) |
| 13. | (Trans-R,R-1,2-diaminocyclohexane)-oxalato-trans-bis(trifluoro-acetato)platinum(IV).H$_2$O | 22.76(22.46) | 2.33(2.49) | 4.52(4.36) |
| 14. | Trans-diacetato(trans-R,R-1,2-diaminocyclohexane)malonatoplatinum(IV) | 29.25(30.35) | 4.44(4.32) | 4.99(5.15) |
| 15. | Trans-diacetato(trans-S,S-1,2-diaminocyclohexane)malonatoplatinum(IV) | 29.26(30.35) | 4.38(4.32) | 4.89(5.15) |
| 16. | Trans-diacetato(cis-1,2-diamino-cyclohexane)malonatoplatinum(IV) | 30.34(29.48) | 4.56(4.15) | 4.74(5.29) |
| 17. | (Trans-R,R-1,2-diaminocyclohexane)-malonato-trans-bis(trifluoro-acetato)platinum(IV).2H$_2$O | 22.70(23.17) | 2.32(2.97) | 4.37(4.16) |
| 18. | Trans-diacetato(trans-R,R-1,2-diaminocyclohexane)tartronato-platinum(IV) | 26.46(26.85) | 4.06(4.47) | 5.18(4.82) |
| 19. | Trans-diacetato(trans-R,R-1,2-diaminocyclohexane)(ketomalonato)platinum(IV) | 25.41(25.66) | 4.17(3.92) | 5.30(4.99) |
| 20. | Trans-diacetato(trans-R,R-1,2-diaminocyclohexane)(methylmalonato)-platinum(IV) | 30.64(30.93) | 4.61(4.41) | 5.09(5.15) |
| 21. | (1,1-cyclobutanedicarboxylato)-trans-diacetato(trans-R,R,-1,2-diaminocyclohexane)platinum(IV) | 33.48(33.74) | 4.61(4.57) | 4.74(4.92) |
| 22. | (1,1-cyclobutanedicarboxylato)-trans-diacetato(trans-S,S-1,2-diaminocyclohexane)platinum(IV) | 33.84(33.74) | 4.48(4.57) | 4.57(4.92) |
| 23. | (1,1-cyclobutanedicarboxylato)-trans-diacetato(trans-R,R-1,2-diaminocyclohexane)platinum(IV) | 33.86(33.74) | 4.48(4.57) | 4.72(4.92) |
| 24. | (1,1-cyclobutanedicarboxylato)-trans-R,R,-1,2-diaminocyclohexane trans-bis(trifluoroacetato)-platinum(IV) | 28.54(28.36) | 2.98(2.95) | 4.04(4.13) |

Trans-diacetato-(trans-R,R-1,2-diaminocyclohexane) malonato-platinum(IV) (complex no. 14 in Table 1) was synthesized by using the following multistep procedure. Potassium tetrachloroplatinum(II) (20.76 g, 50 mmol) was dissolved in deionized water (500 ml) and filtered. To the filtrate was then added potassium iodide (83 g, 0.5 mol in 50 ml of water) and allowed to stir for 5 min. To this solution trans-R,R-1,2-diaminocyclohexane (trans-R,R-DACH) (5.7 g, 0.5 mol in 10 ml of water) was added. A yellow precipitate formed immediately and the reaction mixture was left stirring for 30 min. at room temperature. The water insoluble trans-R,R-DACH-diiodoplatinum(II) was collected by filtration and washed successively with water, dimethylformamide, ethanol, and ether. The final product was dried in a vacuum (yield 95%).

The trans-R,R-DACH-diiodoplatinum(II) (4.5 g, 8 mmol) was mixed with a slightly less than equimolar amount of silver sulfate (2.44 g, 7.8 mmol) in water and the reaction mixture was stirred for 24 hrs in the dark at room temperature. The water soluble aqua-trans-R,R-DACH-sulfatoplatinum(II) was removed from silver chloride precipitate by filtration and was evaporated to dryness at 40° C. under reduced pressure using a rotary evaporator. The final product was recrystallized from water. Aqua-trans-R,R-DACH-sulfato-platinum(II) complex (1.692 g, 4 mmol) was dissolved in 50 ml of water, and a solution of sodium malonate (prepared in situ by mixing 1.6 ml of 5 N NaOH and 0.416 g of malonic acid in 20 ml of water) was added. The reaction mixture was left stirring at room temperature for 24 hrs. The off-white precipitate was separated by filtration. The crude product was recrystallized from water to give white crystals of trans-R,R-DACH-malonato-platinum(II) (yield=85%).

Trans-R,R-DACH-malonatoplatinum(II) (1.233 g, 3 mmol) was suspended in water (100 ml), to which was then added in small portions 30% aqueous hydrogen peroxide (10 ml) at 70° C. on a water bath under stirring for one hr, followed by stirring overnight at room temperature. The final clear solution was filtered and the filtrate was evaporated to dryness under reduced pressure at room temperature. The light yellow solid was redissolved in 30 ml water, filtered and the volume of the filtrate was reduced to about 5 ml which was treated with 100 ml acetone. The white precipitate of trans-R,R-DACH-dihydroxomalonatoplatinum(IV) was recovered by filtration, washed with a small portion of ethanol and dried under vacuum (yield=90%). Finally, trans-R,R-DACH-dihydroxomalonato platinum(IV) (0.89 g, 2 mmol) was suspended in 100 ml $CHCl_3$ and 10 ml of acetic anhydride was added. The mixture was left stirring for 5 hrs at room temperature. Methanol (100 ml) was added to the mixture to give a clear light yellow solution which was kept on stirring for an additional 1 hr, filtered and the filtrate was evaporated to dryness under reduced pressure at room temperature. The final product was redissolved in 30 ml of methanol, filtered and the filtrate was treated with 100 ml ether to give a white precipitate which was collected on a filter paper (yield=95%).

By using the above mentioned procedure the complexes 1-13 and 15-24 in Table 1 were also synthesized. Infrared NMR spectra for these complexes are given in Table 2 below.

TABLE 2

| Spectroscopic Data of DACH—Pt(IV) Complexes | | | | |
|---|---|---|---|---|
| Complex | $IR^a$, $Cm^{-1}$ | | | $^{195}Pt^b$ |
| No | $v(N-H)$ | $v_{as}(C-O)$ | $v_s(C-O)$ | δ, ppm |
| 1 | 3160, 3080 | 1619 | 1357, 1287 | |
| 2 | 3160, 3080 | 1600 | 1350, 1270 | |
| 3 | 3160, 3080 | 1608 | 1355, 1270 | |
| 4 | 3160, 3080 | 1655, 1614 | 1360, 1160 | +1893 |
| 5 | 3161, 3076 | 1642, 1622 | 1362, 1186 | |
| 6 | 3160, 3080 | 1606 | 1342, 1285 | |
| 7 | 3160, 3080 | 1606 | 1342, 1285 | +1846 ($H_2O$) |
| 8 | 3160, 3080 | 1619 | 1360, 1272 | +1840 (MeOH) |
| 9 | 3170, 3080 | 1690, 1629 | 1342, 1165 | |
| 10 | 3160, 3080 | 1659 | 1353, 1277 | |
| 11 | 3160, 3080 | 1650 | 1343, 1271 | |
| 12 | 3160, 3080 | 1680 | 1355, 1276 | |
| 13 | 3160, 3075 | 1701, 1596 | 1344, 1162 | |
| 14 | 3160, 3080 | 1612 | 1342, 1285 | +1755 ($H_2O$) |
| 15 | 3160, 3090 | 1616 | 1346, 1284 | |
| 16 | 3160, 3080 | 1619 | 1360, 1272 | |
| 17 | 3170, 3070 | 1705, 1600 | 1345, 1150 | |
| 18 | 3171, 3071 | 1709, 1647 | 1359, 1279 | |
| 19 | 3171, 3078 | 1705, 1657 | 1360, 1288 | +1576 (MeOH) |
| 20 | 3170, 3080 | 1619 | 1348, 1263 | +1798 (MeOH) |
| 21 | 3160, 3080 | 1618 | 1350, 1280 | +1750 (acetone) |
| 22 | 3160, 3090 | 1610 | 1350, 1280 | |
| 23 | 3160, 3080 | 1620 | 1385, 1274 | +1840 (MeOH) |
| 24 | 3170, 3080 | 1690, 1624 | 1332, 1447 | |

$^a$Infrared spectra are recorded as KBr pellets, and band positions are givin in $cm^1$
$^b$ $^{195}Pt$ chemical shifts are relative to $Na_2PtCl_6$ peak in $D_2O$ at 0.0 ppm Certain ethylenediamine platinum(IV) complexes were synthesized as indicated below. In this section, the following abbreviations are used: CDDP, cis-diamminedichloroplatinum(II); en, ethylenediamine; Mal, malonic acid; CBDCA, 1,1-cyclobutanedicarboxylic acid; DMF, N,N-dimethylformammide; IR, infrared; NMR, nuclear magnetic resonance; $IC_{50}$, concentration of drug required to inhibit cell growth by 50%.

Silver sulfate, CBDCA, Mal, cyclobutanecarboxylic acid ($C_4H_7COOH$), cyclopentanecarboxylic acid ($C_5H_9COOH$), cyclohexanecarboxylic acid ($C_6H_{11}COOH$), and trifluoroacetic anhydride (($CF_3CO$)) were obtained from Aldrich Chemical Co. (Milwaukee, Wis.) while en and acetic anhydride (($CH_3CO)_2O$) were obtained from Fisher Scientific Co. (Houston, Tex.). $K_2PtCl_4$ was purchased from Johnson Matthey (Seabrook, N.H.). All chemicals obtained from commercial suppliers were used as received.

Pt(en)$I_2$. An aqueous solution of $K_2PtCl_4$ (4.15 g, 10 mmol) was treated with KI (6.6 g, 100 mmol) and stirred for 10 min at room temperature. One equivalent of ethylenediamine was added dropwise to the resulting $K_2PtI_4$ solution. Upon stirring for another 5 min, the Pt(en)$I_2$ precipitate was filtered, washed extensively with water, and recrystallized from a $DMF/H_2O$ mixture. After washing with water, methanol and diethyl ether, the final product was dried in vacuo. Yield, 95%.

Pt(en)($SO_4$)($H_2O$). To a Pt(en)$I_2$ (2.38 g, 4.7 mmol) suspension in 200 ml of $H_2O$ in a flask wrapped with aluminum foil was added 500 ml of silver sulfate solution (1.40 g, 4.5 mmol) and 50 ml of acetone. The mixture was stirred overnight. After removal of silver iodide by filtration through Celite, the filtrate was evaporated to dryness at 35° C. The residue was washed with acetone and dried in vacuo. Pt(en)($SO_4$)($H_2O$) was obtained as a bright yellow solid, and the yield was quantitative. Anal. Calc. for $C_2H_{10}N_2O_5SPt$: C, 6.50; H, 2.73; N, 7.79. Found: C, 6.93; H, 2.25; N, 7.02.

$Pt^{II}$(en)(X) (X=CBDCA or Mal) and Pt(en)$X^1X^2$ ($X^1$ and $X^2$=Cl, $OCOC_4H_7$, $OCOC_5H_9$, or $OCOC_6H_{11}$). The general synthetic procedures for these complexes are the same; therefore, only the preparation of $Pt^{II}$(en)(CBDCA) is described here as an example. Pt(en)($SO_4$)($H_2O$)(1.11 g, 3 mmol) was dissolved in 50 ml of water, and 20 ml of sodium 1,1-cyclobutanedicarboxylte (prepared in situ by mixing 6 ml of 1 N NaOH and 0.43 g of CBDCA (3 mmol)) was added. After stirring overnight, the volume of the reaction mixture was reduced to 3 ml under reduced pressure. The precipitate was collected with filter and washed with acetone. The crude product was redissolved in 800 ml of water and filtered through Celite and the filtrate was evaporated to 2 ml under reduced pressure. The crystalline solid was collected with filter and washed with water, acetone, and diethyl ether. The final product, $Pt^{II}$(en)(CBDCA), was dried in vacuo. Yield, 75%.

$Pt^{IV}$(en)(X)(OH)$_2$ and $Pt^{IV}$(en)$X^1X^2$(OH)$_2$. Addition of 10 ml of 30% $H_2O_2$ to an aqueous solution of partially dissolved $Pt^{II}$(en)(CBDCA) (0.80 g, 2 mmol) produced a clear solution initially, which was then followed by the appearance of a white precipitate. After stirring at room temperature overnight, the resulting precipitate was filtered, washed with water, acetone and diethyl ether, and dried in vacuo. $Pt^{IV}$(en)(CBDCA)(OH)$_2$ was obtained as a white solid. Yield, 76%.

All the trans-dihydroxoplatinum(IV) complexes were prepared in a manner similar to that described above.

$Pt^{IV}$(en)(X)$A_2$ and $Pt^{IV}$(en)$X^1X^2Y^1Y^2$, where $Y^1$ and $Y^2$ =$OCOCH_3$ or $OCOCF_3$. To a $Pt^{IV}$(en)(CBDCA)-(OH)$_2$ suspension (0.30 g, 0.7 mmol) in 50 ml of $CH_2Cl_2$ was added 5 ml of acetic anhydride. The mixture was stirred for 2 days. The solvent was removed by evaporation under reduced pressure and the residue was recrystallized from methanol. The final product, $Pt^{IV}$(en)(CBDCA)($OCOCH_3$)$_2$, was dried in vacuo. Yield, 68%.

$Pt^{IV}$(en)(CBDCA)($OCOCF_3$)$_2$ was prepared by using the above-mentioned procedure, starting with $Pt^{IV}$(en)(CBDCA)(OH)$_2$ and ($CF_3CO$)$_2O$.

The remaining complexes [trans-diacetatoplatinum-(IV) and trans-bis(trifluoroacetato)platinum(IV)] listed in Table 5 were prepared in a manner similar to that described above.

Elemental analysis data is given in Table 3. Infrared and NMR spectra for these complexes are given in Table 4.

TABLE 3

Elemental Analysis of Ethylenediamine Platinum(IV) Complexes

| Complex No. | Complex | Found (%) C | H | N | Calc. (%) C | H | N |
|---|---|---|---|---|---|---|---|
| 25 | $Pt^{IV}(en)(CBDCA)(OCOCH_3)_2$ | 28.09 | 4.05 | 5.15 | 27.97 | 3.91 | 5.43 |
| 26 | $Pt^{IV}(en)(CBDCA)(OCOCF_3)_2$ | 22.91 | 2.16 | 4.31 | 23.12 | 2.26 | 4.49 |
| 27 | $Pt^{IV}(en)(Mal)(OCOCH_3)_2$ | 22.54 | 3.45 | 5.90 | 22.74 | 3.39 | 5.89 |
| 28 | $Pt^{IV}(en)(Mal)(OCOCF_3)_2$ | 18.36 | 1.73 | 4.75 | 18.53 | 1.73 | 4.80 |
| 29 | $Pt^{IV}(en)Cl_2(OCOCH_3)_2$ | 16.14 | 2.99 | 6.18 | 16.22 | 3.18 | 6.31 |
| 30 | $Pt^{IV}(en)Cl_2(OCOCF_3)_2$ | 12.90 | 1.73 | 4.95 | 13.05 | 1.46 | 5.07 |
| 31 | $Pt^{IV}(en)(OCOC_4H_7)_2(OCOCH_3)_2$ | 33.43 | 4.81 | 4.88 | 33.62 | 4.94 | 4.90 |
| 32 | $Pt^{IV}(en)(OCOC_4H_7)_2(OCOCF_3)_2$ | 27.99 | 2.98 | 4.00 | 28.28 | 3.26 | 4.12 |
| 33 | $Pt^{IV}(en)(OCOC_5H_9)_2(OCOCH_3)_2$ | 36.01 | 5.48 | 4.60 | 36.06 | 5.38 | 4.67 |
| 34 | $Pt^{IV}(en)(OCOC_5H_9)_2(OCOCF_3)_2$ | 30.27 | 3.52 | 3.91 | 30.56 | 3.70 | 3.96 |
| 35 | $Pt^{IV}(en)(OCOC_6H_{11})_2(OCOCH_3)_2$ | 38.33 | 5.72 | 4.42 | 38.28 | 5.78 | 4.46 |
| 36 | $Pt^{IV}(en)(OCOC_6H_{11})_2(OCOCF_3)_2$ | 32.43 | 3.87 | 3.75 | 32.66 | 4.11 | 3.81 |

TABLE 4

Infrared and NMR Spectroscopic Data for Ethylenediamine Platinum(IV) Complexes[1]

| Complex No. | IR, cm$^{-1}$ $\nu$N—H | $\nu$C=O | $\nu$C—O | $\nu$C—F | NMR, ppm $^{13}$C | $^{195}$Pt |
|---|---|---|---|---|---|---|
| 25 | 3177–3042 | 1620 | 1348, 1276 | | 181.7 | 1727 |
| 26 | 3189–3104 | 1706, 1630 | 1336, 1209 | 1153 | 180.9, 184.8 | 1768 |
| 27 | 3179–3084 | 1617 | 1344, 1272 | | 177.2, 181.9 | 1706 |
| 28 | 3214–3166 | 1706, 1638 | 1360, 1205 | 1153 | 172.0[2] | 1796[3] |
| 29 | 3190 | 1620 | 1361, 1349, 1272 | | 179.5[2] | 1028[3] |
| 30 | 3171, 3082 | 1720, 1601 | 1376, 1208 | 1151 | 165.4[4] | 923[5] |
| 31 | 3204 | 1619 | 1349, 1273 | | 182.5, 185.3 | 1770 |
| 32 | 3170–3155 | 1712, 1624 | 1340, 1253 | 1163 | 184.3[6] | 1827[5] |
| 33 | 3211–3177 | 1619 | 1351, 1303(sh), 1273 | | 182.5, 186.4 | 1806[5] |
| 34 | 3189–3144 | 1699, 1623 | 1339–1319, 1298 | 1162 | 185.5, 187.1[6] | 1782[5] |
| 35 | 3175 | 1616 | 1351–1338, 1308(sh), 1269 | | 181.8, 185.0[6] | 1796[5] |
| 36 | 3179–3155 | 1711, 1624 | 1371–1351, 1315, 1258 | 1160 | 185.1[6] | 1778[5] |

[1]Infrared spectra were recorded as KBr pellets. sh = shoulder. $^{195}$Pt NMR spectra were recorded in H$_2$O or CH$_3$OH. All $^{195}$Pt chemical shifts were referenced to aqueous Na$_2$PtCl$_6$. $^{13}$C NMR spectra were recorded in D$_2$O with CD$_3$OD as reference (49.00 ppm).
[2]Measured in (CD$_3$)$_2$SO.
[3]Measured in (CH$_3$)$_2$SO.
[4]Quartet. J$_{(C=O)-F}$ = 38.9 Hz. Measured in CD$_3$OD.
[5]Measured in CH$_3$OH.
[6]Measured in CD$_3$OD.

Antitumor Activity

EXAMPLE 1

Cisplatin-sensitive L1210/0 cells ($1 \times 10^5$ cells/mouse) were injected intraperitoneally in male BDF1 mice on day 0, and a DACH complex, in an aqueous medium, was administered intraperitoneally at dose levels ranging from 1.56 to 200 mg/kg on days 1, 5 and 9. the median life spans of control (C) and treated (T) animals were determined, and the percent T/C at the optimal dose calculated as an indicator of antitumor efficacy. (Percent T/C is the median survival time of treated mice/median survival time of control mice x 100.) From the efficacy data, the optimal dose was ascertained. Table 5 gives the percent T/C values for the complexes tested, as well as the number of mice cured where applicable.

TABLE 5

Efficacy of Complexes Against L1210/0

| Complex No. | Optimal dose (mg/kg/inj) | % T/C at opt. dose |
|---|---|---|
| 1 | 200 | 206 |
| 2 | 200 | 194 |
| 3 | 200 | 182 |
| 4 | 25 | 218 (1/5) |
| 6 | 100 | 206 |
| 7 | 50 | 182 (2/5) |
| 9 | 25 | 241 (1/5) |
| 10 | 50 | 171 |
| 11 | 50 | 135 |
| 12 | 100 | 159 |
| 13 | 50 | >700 (3/5) |
| 14 | 200 | 194 |
| 15 | 200 | 171 |
| 16 | 200 | 206 (1/5) |
| 17 | 100 | 218 |
| 21 | 200 | 112 |
| 22 | 200 | 112 |
| 23 | 200 | 112 |
| 24 | 200 | 253 (1/5) |
| Cisplatin | 5 | 300 |

TABLE 5-continued

Efficacy of Complexes Against L1210/0

| Complex No. | Optimal dose (mg/kg/inj) | % T/C at opt. dose |
|---|---|---|
| Carboplatin | 75 | 147 |

Figures in parentheses are number of animals cured/number of animals treated.

EXAMPLE 2

Cisplatin-resistant L1210/cisplatin cells ($1 \times 10^5$ cells/mouse) were injected intraperitoneally in male BDF1 mice on day 0, and a DACH complex, in an aqueous medium, was administered intraperitoneally at dose levels ranging from 1.56 to 200 mg/kg on days 1, 5 and 9. The median life spans of control (c) and treated (T) animals were determined, and the percent T/C calculated as an indicator of antitumor efficacy. From the efficacy data, the optimal dose was ascertained. Table 6 gives the optimal dose and percent T/C values for the complexes tested.

TABLE 6

Efficacy of complexes against L1210/cisplatin

| Complex No. | Optimal dose (mg/kg/inj) | % T/C at opt. dose |
|---|---|---|
| 4 | 25 | 148 |
| 6 | 50 | 157 |
| 9 | 25 | 224 |
| 13 | 50 | 176 |
| 14 | 200 | 138 |
| 24 | 100 | 205 |
| Cisplatin | 5 | 100 |
| Carboplatin | 75 | 111 |

EXAMPLE 3

Ethylenediamine platinum complexes were dissolved in water or 95% ethanol and their antitumor activity determined in vitro against murine leukemia L1210/0 cells (final ethanol concentration 0.25%). Briefly, cells were cultured in RPMI 1640 medium containing 10% fetal calf serum, and cytotoxicity was determined after continuous drug exposure for 72 h by an MTT assay. Drug concentration was plotted against cell survival, and $IC_{50}$ values (drug concentration giving 50% survival) were determined directly from the plot.

As shown in Table 7, all the compounds displayed antitumor activity, with $IC_{50}$ values in the range of 0.1 to 93 μM. Carboxylato groups in the axial position appear to have a substantial influence on antitumor activity for equatorial mondentate bis-carboxylato analogs but less influence for bidentate carboxylato analogs.

TABLE 7

Ethylenediamine Platinum (IV) Complexes and Their Antitumor Activity Against L1210/0 Leukemia Cells

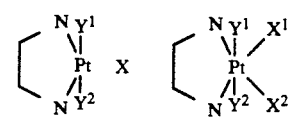

| Complex No. | $Y^1$ and $Y^2$ | X | $X^1$ and $X^2$ | $IC_{50}$ (μM) |
|---|---|---|---|---|
| 25 | $OCOCH_3$ | CBDCA | | 92.5 |
| 26 | $OCOCF_3$ | CBDCA | | 33.6 |
| 27 | $OCOCH_3$ | Mal | | 73.2 |
| 28 | $OCOCF_3$ | Mal | | 39.3 |
| 29 | $OCOCH_3$ | | Cl | 7.1 |

TABLE 7-continued

Ethylenediamine Platinum (IV) Complexes and Their Antitumor Activity Against L1210/0 Leukemia Cells

| Complex No. | $Y^1$ and $Y^2$ | X | $X^1$ and $X^2$ | $IC_{50}$ (μM) |
|---|---|---|---|---|
| 30 | $OCOCF_3$ | | Cl | 3.8 |
| 31 | $OCOCH_3$ | | $OCOC_4H_7$ | 85.6 |
| 32 | $OCOCF_3$ | | $OCOC_4H_7$ | 0.11 |
| 33 | $OCOCH_3$ | | $OCOC_5H_9$ | 39.3 |
| 34 | $OCOCF_3$ | | $OCOC_5H_9$ | 0.27 |
| 35 | $OCOCH_3$ | | $OCOC_6H_{11}$ | 8.3 |
| 36 | $OCOCF_3$ | | $OCOC_6H_{11}$ | 0.14 |

Compositions in accordance with the present invention can suitably include a pharmaceutically effective amount of one or more platinum complexes in accordance with the present invention, and a pharmaceutically acceptable carrier, such as, for example, water, saline, or dextrose solution. Compositions in accordance with the present invention will contain between about 0.001% and about 99% by weight active complexes, preferably between about 0.001% and about 10%.

Methods in accordance with the present invention comprise administering to a mammal an effective amount of the compounds or complexes described above. The administering step can suitably be parenteral and by intravenous, intraarterial, intramuscular, intralymphatic, intraperitoneal, subcutaneous, intrapleural, or intrathecal injection, or by topical application or oral dosage. Such administration is preferably repeated on a timed schedule until tumor regression or disappearance has been achieved, and may be used in conjunction with other forms of tumor therapy such as surgery or chemotherapy with different agents. The dose administered of a complex in accordance with the present invention can be between about 0.5 and about 100 mg/kg of body weight of the subject to which it is administered.

The description and examples given in this patent are intended to illustrate the present invention. They are not intended to be an exhaustive list of all possible specific embodiments of the present invention. Those skilled in the art will recognize that modifications could be made to the specific embodiments listed here which would still be within the scope of the present invention.

We claim:

1. A platinum(IV) complex having the formula

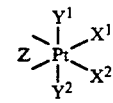

or a stereoisomer thereof, where $X^1$ and $X^2$ are carboxylato or are jointly dicarboxylato, where $Y^1$ and $Y^2$ are carboxylato, and where Z is a bidentate ligand selected from the group consisting of diaminocyclohexane and ethylenediamine.

2. The complex of claim 1, where $X^1$ and $X^2$ are carboxylato having between about 1–10 carbon atoms each or are jointly dicarboxylato having between about 2–20 carbon atoms, and where $Y^1$ and $Y^2$ are carboxylato having between about 1-10 carbon atoms each.

3. The complex of claim 1, where $X^1$ and $X^2$ are selected from the group consisting of
    acetato,
    trifluoroacetato, and
    cyclobutanecarboxylato,
or are jointly selected from the group consisting of
    oxalato,
    malonato,
    methylmalonato,
    ketomalonato,
    tartronato, and
    1,1-cyclobutanedicarboxylato.

4. The complex of claim 1, where $Y^1$ and $Y^2$ are selected from the group consisting of
    acetato,
    trifluoroacetato, and
    cyclobutanecarboxylato.

5. An antitumor composition which includes (a) an amount effective to inhibit neoplastic cell growth of a platinum(IV) complex having the formula

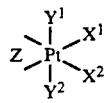

or a stereoisomer thereof where $X^1$ and $X^2$ carboxylato or are jointly dicarboxylato, where $Y^1$ and $Y^2$ are carboxylato, and where Z is a bidentate ligand selected from the group consisting of diaminocyclohexane and ethylenediamine, and (b) a pharmaceutically acceptable carrier.

6. The composition of claim 5, where $X^1$ and $X^2$ are carboxylato having between about 1-10 carbon atoms each or are jointly dicarboxylato having between about 2-20 carbon atoms, and where $Y^1$ and $Y^2$ are carboxylato having between about 1-10 carbon atoms each.

7. The composition of claim 5 where $X^1$ and $X^2$ are selected from the group consisting of
    acetato,
    trifluoroacetato, and
    cyclobutanecarboxylato,
or are jointly selected from the group consisting of
    oxalato,
    malonato,
    methylmalonato,
    ketomalonato,
    tartronato, and
    1,1-cyclobutanedicarboxylato.

8. The composition of claim 5, where $Y^1$ and $Y^2$ are selected from the group consisting of
    acetato,
    trifluoroacetato, and
    cyclobutanecarboxylato.

9. A method of inhibiting neoplastic cell growth, including the step of administering to a mammal an amount effective to inhibit neoplastic cell growth of a platinum(IV) complex having the formula

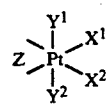

or a stereoisomer thereof, where $X^1$ and $X^2$ are carboxylato or are jointly dicarboxylato, where $Y^1$ and $Y^2$ are carboxylato, and where Z is a bidentate ligand selected from the group consisting of diaminocyclohexane and ethylenediamine.

10. The method of claim 9, where $X^1$ and $X^2$ are carboxylato having between about 1-10 carbon atoms each or are jointly dicarboxylato having between about 2-20 carbon atoms, and where $Y^1$ and $Y^2$ are carboxylato having between about 1-10 carbon atoms each.

11. The method of claim 9, where $X^1$ and $X^2$ are selected from the group consisting of
    acetato,
    trifluoroacetato, and
    cyclobutanecarboxylato,
or are jointly selected from the group consisting of
    oxalato,
    malonato,
    methylmalonato,
    ketomalonato,
    tartronato, and
    1,1-cyclobutanedicarboxylato.

12. The method of claim 9, where $Y^1$ and $Y^2$ are selected from the group consisting of
    acetato,
    trifluoroacetato, and
    cyclobutanecarboxylato.

* * * * *

REEXAMINATION CERTIFICATE (2815th)

United States Patent [19]

Khokhar et al.

[11] B1 5,288,887

[45] Certificate Issued Mar. 12, 1996

[54] DIAMINE PLATINUM(IV) COMPLEXES HAVING MIXED CARBOXYLATE LIGANDS AS ANTITUMOR AGENTS

[75] Inventors: Abdul R. Khokhar; Zahid H. Siddik; Salaam Al-Baker, all of Houston, Tex.

[73] Assignee: Board of Reagents, The University of Texas System, Austin, Tex.

Reexamination Request:
No. 90/003,725, Feb. 15, 1995

Reexamination Certificate for:
Patent No.: 5,288,887
Issued: Feb. 22, 1994
Appl. No.: 978,788
Filed: Nov. 19, 1992

Related U.S. Application Data

[63] Continuation-in-part of Ser. No. 927,701, Aug. 7, 1992, which is a continuation-in-part of Ser. No. 624,795, Dec. 7, 1990, abandoned, which is a division of Ser. No. 274,824, Nov. 22, 1988, Pat. No. 5,041,578.

[51] Int. Cl.$^6$ .......................... C07F 15/00; A61K 31/28
[52] U.S. Cl. .......................... 556/137; 540/465; 514/184; 514/185; 514/492

[58] Field of Search .......................... 556/137; 540/465; 514/184, 185, 492

[56] References Cited

U.S. PATENT DOCUMENTS

| | | | |
|---|---|---|---|
| 5,041,578 | 8/1991 | Khokhar et al. | 556/137 |
| 5,072,011 | 12/1991 | Abrams et al. | 556/137 |
| 5,288,887 | 2/1994 | Khokhar et al. | 556/137 |
| 5,318,962 | 6/1994 | Khokhar et al. | 514/184 |

FOREIGN PATENT DOCUMENTS 0328274  8/1989  European Pat. Off. .

*Primary Examiner*—José G. Dees

[57] ABSTRACT

Platinum(IV) complexes with mixed carboxylato ligands having the formula:

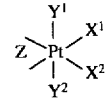

where $X^1$ and $X^2$ are carboxylato, or are jointly dicarboxylato, where $Y^1$ and $Y^2$ are carboxylato, and where Z is either diaminocyclohexane or ethylenediamine, have been found to have desirable antitumor activity, as well as relatively low levels of toxicity.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-12 are cancelled.

* * * * *